(12) United States Patent
Gill et al.

(10) Patent No.: US 6,936,420 B2
(45) Date of Patent: Aug. 30, 2005

(54) METHOD OF AMPLIFICATION OF ONE OR MORE DNA SEQUENCES IN A DNA CONTAINING SAMPLE AND METHODS OF INVESTIGATING SUCH SAMPLES

(75) Inventors: Peter David Gill, Birmingham (GB); Javaid Iqbal Hussain, Birmingham (GB); Adam Spencer Long, Birmingham (GB); Gillian Tully, Lambeth (GB)

(73) Assignee: The Secretary of State for the Home Department, Birmingham (GB)

( * ) Notice: Subject to any disclaimer, the term of this patent is extended or adjusted under 35 U.S.C. 154(b) by 487 days.

(21) Appl. No.: 10/174,197

(22) Filed: Jun. 17, 2002

(65) Prior Publication Data

US 2003/0027190 A1 Feb. 6, 2003

(30) Foreign Application Priority Data

Jun. 15, 2001 (GB) .............................................. 0114639

(51) Int. Cl.⁷ ............................. C12Q 1/68; C12P 19/34
(52) U.S. Cl. ......................................... 435/6; 435/91.2
(58) Field of Search .................................. 435/6, 91.2

(56) References Cited

U.S. PATENT DOCUMENTS 5,705,366 A   1/1998  Backus
6,040,166 A   3/2000  Erlich et al.

FOREIGN PATENT DOCUMENTS

EP   0 648 845   4/1995
EP   0 694 617   1/1996
WO   01/07640   *  2/2001   ............ C12Q/1/00

OTHER PUBLICATIONS

Wu et al., "The Effect of Temperature and Oligonucleotide Primer Length on the Specificity and Efficiency of Amplification by the Polymerase Chain Reaction", DNA and Cell Biology, vol. 10, No. 3, pp. 233–238, Apr. 1991.

Sugimoto et al., "Quanatative Detection of DNA by Coamplification Polymerase Chain Reaction: A wide Detectable Range Controlled by the Thermodynamic Stability of Primer Template Duplexes", Analytical Biochemistry, vol. 211, No. 1, pp. 170–172, May 1993.

Backus et al., "Method of Amplification Using Intermediate Renaturation Step", Biotechnology Advances Research Reviews and Patent Abstracts vol. 15 No. 2, 1997 Abstract.

* cited by examiner

Primary Examiner—Kenneth R. Horlick
(74) Attorney, Agent, or Firm—Merchant & Gould P.C.

(57) ABSTRACT

A method of amplification of one or more DNA sequences in a DNA containing sample, and methods of investigating such samples are provided in which an improved amplification cycling regime is used. The regime features a first phase and a second phase, the first phase including a denaturation temperature step, followed by an annealing temperature step, followed by a corrected annealed primer extension temperature step, these steps being followed by an annealing temperature step, corrected annealed primer extension temperature step prior to any further denaturation temperature steps being applied. Increased amplification from a given number of amplification cycles and maximised sensitivity for the DNA amplification process is achieved as a result.

25 Claims, 4 Drawing Sheets

METHOD OF AMPLIFICATION OF ONE OR MORE DNA SEQUENCES IN A DNA CONTAINING SAMPLE AND METHODS OF INVESTIGATING SUCH SAMPLES

This invention concerns improvements in and relating to analysis of DNA, and particularly, but not exclusively to techniques for amplifying DNA for analysis.

In forensic investigations, and analysis for other purposes, it is known to make use of bi-allelic markers or single nucleotide polymorphisms (SNPs). SNPs represent single base locations where variations between the sequence for one being and another can occur. A SNP may for instance be the presence of G or C, or of A or T, in the sequence of an individual, with some of the individuals having one of the options and other individuals having the other option. By considering a large number of such SNPs at different loci, a set of SNP results for an individual can be obtained which is useful for investigative purposes. The results may be compared with the results from another sample, with the statistical occurrence of that set of results within the population as a whole or used in other ways.

A key part of the investigative process is the amplification of the DNA of interest from the low levels present in the collected sample up to levels where the SNP identities can be inspected. This is particularly the case where the initial sample is small as a whole or the contribution of the party of interest to the sample is small relative to the whole.

Successful but selective annealing and extension of the DNA of interest present in the original sample and during the early amplification cycles is most important as each copy generated in the early cycles results in a massive number in the later cycles.

The present invention has amongst its aims to provide increased amplification from a given number of amplification cycles, of the DNA of interest. The present invention has amongst its aims to provide maximised sensitivity for a DNA amplification process. The present invention has amongst its aims to produce more copies of the DNA of interest within a given time period and/or to produce a given number of copies in a shorter time period.

According to a first aspect of the invention we provide a method of amplifying one or more DNA sequences in a DNA containing sample, the one or more sequences including a single nucleotide polymorphism, the method including contacting the sample with a first set of primers and providing amplification of the DNA sequences using the primers to give an amplified product, wherein the amplification includes a first phase and a second phase, the first phase including exposing the DNA sample to a denaturation temperature step, followed by an annealing temperature step followed by a correctly annealed primer extension temperature step, these steps being followed, at least, by an annealing temperature step, followed by a correctly annealed primer extension temperature step, these steps occurring prior to exposing the DNA sample to a further denaturation temperature step, the second phase providing one or more cycles of a denaturation temperature step followed by an annealing temperature step and extension temperature step.

According to a second aspect of the invention we provide a method of amplifying DNA in a DNA containing sample, the method including contacting the sample with a first set of primers and providing amplification of the DNA using the primers to give an amplified product, wherein the amplification includes a first phase and a second phase, the first phase including exposing the DNA to a denaturation temperature, followed by an annealing temperature followed by a correctly annealed primer extension temperature, these being followed, at least, by an annealing temperature, followed by a correctly annealed primer extension temperature, these temperatures occurring prior to exposing the DNA to a further denaturation temperature.

Preferably the DNA is one or more DNA sequences in the DNA containing sample. The one or more sequences may included a single nucleotide polymorphism.

The method may include contacting the sample with a first set of primers.

Preferably the temperatures are temperature steps, having a temperature profile and a duration.

Preferably the second phase provides one or more cycles of a denaturation temperature followed by an annealing temperature and extension temperature.

The first and/or second aspects of the invention may include one or more of the following features, options or possibilities.

Preferably the correctly annealed primer extension temperature step provides a temperature and/or duration which provides extension of a primer with a pairing base to the single nucleotide polymorphism. Preferably the correctly annealed primer extension temperature step provides a temperature and/or duration which provides for the removal from an annealed state with the DNA of a primer with an equivalent base to the single nucleotide polymorphism.

The sample may be extracted from the collected source. The sample may be a mixture. One or more contributions to the sample may be analysed following amplification. The DNA sequence may be at least 20 bases long. Preferably the sequence incorporates at least one single nucleotide polymorphism.

Preferably the first set of primers includes a forward primer for each sequence being amplified, and at least one reverse primer.

Preferably in the temperature steps, the temperature is substantially constant throughout the duration of that step. Preferably equivalent denaturation and/or annealing and/or extension temperatures are used for the respective steps in each phase.

The denaturation temperature step on the first phase is preferably performed at a temperature of 90 to 98° C. and more preferably 94° C.+/−1° C. and ideally 94° C.+/−0.5° C. Preferably the denaturation temperature step in the first phase lasts for between 20 and 60 seconds, and more preferably 30 seconds+/−5 seconds.

The denaturation temperature step on the second phase is preferably performed at a temperature of 90 to 98° C. and more preferably 94° C.+/−1° C. and ideally 94° C.+/−0.5° C. Preferably the denaturation temperature step in the second phase lasts for between 20 and 60 seconds, and more preferably 30 seconds +/−5 seconds.

The denaturation temperature step on the third phase is preferably performed at a temperature of 90 to 98° C. and more preferably 94° C.+/−1° C. and ideally 94° C.+/−0.5° C. Preferably the denaturation temperature step in the third phase lasts for between 30 and 90 seconds, and more preferably 60 seconds +/−10 seconds.

Preferably an annealing temperature step of the first phase, and ideally all annealing temperature steps of the first phase, employ a temperature of between 55 and 65° C. and more preferably 60° C.+/−1° C. Preferably an annealing temperature step of the first phase, more preferably all the annealing temperature steps in the first phase, have a duration of between 10 and 20 seconds, more preferably 15 seconds +/−1 second.

Preferably a correctly annealed primer extension temperature step of the first phase, more preferably all correctly annealed primer extension temperature steps of the first phase, are performed at a temperature of between 70 and 76° C. and more preferably at 72° C.+/−1° C. Preferably a correctly annealed primer extension temperature step of the first phase, more preferably all correctly annealed primer extension temperature steps of the first phase, are performed for a duration of 10 to 20 seconds and more preferably 15 seconds +/−1 second.

Preferably the first phase includes one or more cycles. Preferably the first phase includes 1 to 10 cycles and more preferably 2 to 6 cycles. A cycle preferably includes a denaturation temperature step, an annealing temperature step, a correctly annealed primer extension temperature step, a further annealing temperature step and a further correctly annealed primer extension step, ideally in that order. The further correctly annealed primer extension temperature step is preferably followed by a still further annealing temperature step and a still further correctly annealed primer extension temperature step. The first phase may include a denaturation temperature step together with between 2 and 6 pairs of an annealing temperature step and a correctly annealed primer extension temperature step which follow on one from another. Preferably the cycles of phase 1 each include only one denaturation temperature step, ideally the first temperature step of the cycle.

Preferably phase 2 includes one or more combined annealing temperature step and extension temperature steps. Preferably the combined annealing temperature step and extension temperature step of phase 2 is performed at a temperature of between 72 and 80° C. and more preferably at 76° C.+/−1° C. Preferably the combined annealing temperature step and extension temperature step of phase 2 is performed for a duration of between 60 and 120 seconds and more preferably 105 seconds +/−5 seconds.

Preferably phase 2 includes two or more cycles and more preferably at least 20 cycles. Phase 2 may include between 25 and 35 cycles and more preferably 29 to 33 cycles.

The cycles of phase 2 may include a denaturation step followed by a combined annealing and extension temperature step. Preferably cycles in phase 2 consist of a denaturation step followed by a combined annealing and extension temperature step.

Preferably phase 3 includes one or more annealing temperature steps. Preferably at least one of the annealing temperature steps of phase 3, more preferably all the annealing temperature steps of phase 3, are performed at 55 to 65° C. and more preferably at 60° C.+/−1° C. Preferably an annealing temperature step of phase 3, more preferably all annealing temperature steps of phase 3, are performed for a duration of between 20 and 45 seconds, and more preferably 30 seconds +/−2 seconds.

Preferably phase 3 includes one or more extension temperature steps. Preferably an extension temperature step of phase 3, more preferably all extension temperature steps of phase 3, are performed at a temperature of 70 to 76° C. and ideally at 72° C.+/−1° C.

Preferably phase 3 includes one or more cycles and ideally between 2 and 5 cycles. Preferably one or more of, and ideally all of the cycles of phase 3, include a denaturation temperature step, an annealing temperature step and an extension temperature step. Preferably the cycles consist of these steps, ideally in the sequence denaturation, annealing, extension.

According to a third aspect of the invention we provide a method of investigating single nucleotide polymorphisms in a DNA containing sample, the method including contacting the DNA containing sample with a first set of primers and amplifying the DNA using those primers to give an amplified product, contacting the amplified product with at least a second set of primers, amplifying the amplified product using those second set of primers to give a further amplified product and examining one or more characteristics of the further amplified product, wherein the amplification to give the amplified product includes a first phase and a second phase, the first phase including exposing the DNA sample to a denaturation temperature step, followed by an annealing temperature step followed by a correctly annealed primer extension temperature step, these steps being followed, at least, by an annealing temperature step, followed by a correctly annealed primer extension temperature step, these steps occurring prior to exposing the DNA sample to a further denaturation temperature step, the second phase providing one or more cycles of a denaturation temperature step followed by an annealing temperature step and extension temperature step and wherein the amplification to give the further amplified product involves a third phase, the third phase providing one or more cycles of a denaturation temperature step followed by an annealing temperature step and extension temperature step.

According to a fourth aspect of the invention we provide a method of investigating a DNA containing sample, the method including contacting the DNA containing sample with a first set of primers and amplifying the DNA using those primers to give an amplified product, contacting the amplified product with at least a second set of primers and amplifying the amplified product using those second set of primers to give a further amplified product and examining one or more characteristics of the further amplified product, wherein the amplification to give the amplified product includes a first phase and a second phase, the first phase including exposing the DNA sample to a denaturation temperature, followed by an annealing temperature followed by a correctly annealed primer extension temperature, these being followed, at least, by an annealing temperature, followed by a correctly annealed primer extension temperature, these occurring prior to exposing the DNA sample to a further denaturation temperature, and wherein the amplification to give the further amplified product involves a third phase, Preferably the investigation is directed towards single nucleotide polymorphisms in the DNA sequence.

Preferably the temperatures are temperature steps, having a temperature profile and a duration.

Preferably the second phase provides one or more cycles of a denaturation temperature followed by an annealing temperature and extension temperature.

Preferably the third phase provides one or more cycles of a denaturation temperature followed by an annealing temperature and extension temperature.

The method of amplifying may be part of a method of investigating single nucleotide polymorphisms in a sample of DNA. The method of investigating may comprise contacting the DNA containing sample with at least one first set of primers, amplifying the DNA using those primers to give an amplified product, contacting at least a portion of the amplified product with at least one second set of primers, amplifying the DNA using those second set of primers to give a further amplified product and examining one or more characteristics of the further amplified product.

In one embodiment of the invention one or more, preferably all, of the first sets of primers may include two forward primers and a reverse primer. One or more, preferably all, of the first sets of primers may consist of two forward and a reverse primer. The forward primers and reverse primer preferably include sequences which anneal to the 3' and 5' sides respectively of the SNP at the locus incorporating the SNP under investigation.

In an alternative embodiment of the invention, one or more, preferably all of the first sets of primers may include a forward primer and a reverse primer. One or more, preferably all of the first sets of primers may consist of one forward primer and one reverse primer. The forward primer and reverse primer preferably include sequences which pair/anneal to the 3' and 5' sides respectively of the SNP at the locus incorporating the SNP under investigation.

The first set of primers may include one or more primers including a locus specific portion and a further portion. Preferably the forward primers are so provided. Preferably the further portion is attached to the 5' end of the locus specific portion, particularly in the case of forward primers. The 3' end of the forward primer is preferably provided with a SNP identifying portion. The further portion is preferably attached to the locus specific portion by a SNP related portion.

In one embodiment of the invention the locus specific portion preferably includes a sequence which matches the sequence of the locus sequence in the vicinity of the SNP under investigation. The match may occur at between 2 to 10 bases to the respective sides of the SNP under investigation. More preferably the sequence matches the locus sequence for the locus sequence adjacent to the SNP under investigation, ideally up to and including the nucleotide before the SNP on the 3' side of the SNP. Preferably the forward primers of a first set of primers are provided with identical sequences for the locus specific portion.

In one embodiment of the invention the SNP identifying portion is preferably a single nucleotide. The SNP identifying portion may be a C for investigating an SNP where the SNP may be a G nucleotide. The SNP identifying portion may be a G nucleotide for investigating an SNP where the SNP may be a C nucleotide. The SNP identifying portion may be a T nucleotide for investigating an SNP where the SNP may be an A nucleotide. The SNP identifying portion may be an A nucleotide for investigating an SNP where the SNP may be a T nucleotide. Preferably the SNP identifying portion for one forward primer of a set is one of C or G or A or T, with the SNP identifying portion of the other forward primer of the set being one of C or G or A or T, but different from the SNP identifying portion of the first forward primer of the set. Preferably the SNP identifying portions are provided to target the two possible variations of the SNP in question, for instance C and T for the primers to investigate G or A for the SNP, C or G for the primers to investigate G or C for the SNP and so on.

Preferably the SNP identifying portion forms the 3' end of the forward primers of the first set.

The further portion preferably includes a sequence which does not match the locus sequence on the locus's 3' side of the locus sequence matching the locus specific portion of the primer. More preferably the sequence does not match the sequence of the locus in the vicinity of the SNP under investigation. Ideally the sequence does not anneal to, and particularly does not match, the sequence of any published part, ideally any part, of the entire DNA sequence of the entity from which the DNA containing the SNP under investigation was obtained, for instance Homo Sapiens. The inability of the sequence of the further portion to amplify human DNA is a particularly preferred feature. Preferably the forward primers of a first set of primers are provided with identical sequences for the further portion.

Preferably the further portion forms the 5' end of the forward primers of the first set.

The further portion of two or more of the forward primers of the first set may have an equivalent sequence. All the forward primers of the first set may be provided with further portions of equivalent sequence.

In a preferred embodiment of the invention, the further portion of at least one of the forward primers of the first set is different from the further portion of at least one of the other forward primers of the first set, at least in part. Preferably the further portion of each forward primer of the first set is different from the further portion of each of the other forward primers of the first set, at least in part. It is preferred that the forward primers are different from one another with respect to at least 25% of the nucleotides forming the further portion of the forward primers. Differences in sequence, ranging between 25% and 100% of the nucleotides forming the further portion of the forward primers may be employed. The differences in sequence may form one or more distinguishing portions. One or more distinguishing portions may be provided as or within the further portion of the forward primers. A distinguishing portion may be provided at the 5' end of the further portion of the forward primer. The distinguishing portion may be provided at the 3' end of the further portion of the forward primer. Preferably the distinguishing portion is provided at an intermediate location within the sequence of the further portion. Preferably a 5' end portion, distinguishing portion and 3' end portion defines the further portion of the forward primers.

The further portion of one or more of the primers in the first set may be provided with one or more portions which correspond with one or more portions in the further portion of one or more of the other primers in the first set. The nucleotides of the further portion of one or more of the forward primers may be equivalent to the nucleotides of one of the other forward primers, outside the distinguishing portion of the further portion. In particular, the 5' end portion and/or 3' portion of the further portion of one or more of the forward primers may be equivalent to the corresponding further portion of one or more of the other forward primers. Preferably all of the forward primers are provided with equivalent 5' end and/or 3' end portions to one another. The equivalent portions may form between 1 and 25% of the sequence of the further portion of the primers. Preferably the equivalent portions form between 10 and 25% of the sequence of the further portions. The reverse primer or primers of the first set may be provided with equivalent portions too.

The SNP related portion is preferably a single nucleotide. The SNP related portion is preferably identical to the SNP identifying portion of that primer. Preferably the two forward primers are provided with SNP related portions which are identical with their respective SNP identifying portions. The SNP related portion may be a C for investigating an SNP where the SNP may be a G nucleotide. The SNP related portion may be a G nucleotide for investigating an SNP where the SNP may be a C nucleotide. The SNP related portion may be a T nucleotide for investigating an SNP where the SNP may be an A nucleotide. The SNP related portion may be an A nucleotide for investigating an SNP where the SNP may be a T nucleotide. Preferably the SNP related portion for one forward primer of a set may be one of C or G or A or T, with the SNP related portion of another primer of the set being one of C or G or A or T, but different to the SNP related portion of the first primer of the set. Preferably the SNP related portions for the primers of a set are provided to match the SNP identifying portion of their respective primers.

Preferably during amplification the SNP related portion results in the amplified copies of the locus incorporating the SNP having an SNP repeat introduced into them. Ideally, the repeat has a base identity identical to that of the SNP.

Preferably the locus specific portion and SNP identifying portion of one of the forward primers anneals to the 3' side of the locus having the SNP under investigation. Preferably the locus specific portion and SNP identifying portion of another, ideally the other, of the forward primers does not anneal to the 3' side of the SNP under investigation. Preferably the annealing primer anneals due to a match between the SNP identifying portion and the SNP site, (for instance C matching to G). Preferably the non-annealing primer does not anneal due to a mismatch between the SNP identifying portion and the SNP site, (for instance, T mis-matching with T).

The SNP under investigation may be a location with variation between individuals of any two bases selected from C or G or A or T nucleotides. For instance, the SNP under investigation may be a location with variation between individuals of either a T or A nucleotide, T or C nucleotide, T or G nucleotide, A or C nucleotide, A or G nucleotide or C or G nucleotide. One possible variation may be investigated at one or more sites, with one or more other potential variations being investigated at one or more other sites.

Two or more SNP's may be investigated using a simultaneous first amplification and/or simultaneous second amplification and/or simultaneous examination of the one or more characteristic of the further amplified product. Preferably at least the first amplification and second amplification are conducted simultaneously for a plurality of SNP investigations. The number of SNP's investigated simultaneously in one or more stages of the process may be greater than 20, preferably greater than 25, more preferably greater than 50 and ideally greater than 100.

The sample may be a sample of DNA extracted from a collected source.

The sample may be contacted with the first primer set by mixing the sample and primers together.

The sample may be a mixture. One or more contributions to the sample may be analysed as the sample itself using the present invention. The mixed sample may include male and female DNA. One of the sexes of DNA, particularly the male, may be present in low concentrations relative to the other sex. For instance, the minor sex DNA contribution may form less than 1% of the sample, potentially less than 0.1% and even less than 0.05%. The sample may contain samples from two or more sources. The method may investigate the minor sample in a mixture from two or more sources. The minor sample may form less than 1% of the mixed sample, potentially less than 0.1% of the mixed sample and even less than 0.05% of the mixed sample.

The investigation may indicate the amount of DNA in a mixed sample from one or more of the sources. The indication may be based on a comparison of the experimentally determined results, for instance the level of a distinctive unit present, compared with a set of calibration results based on investigation of known amounts of DNA in a sample.

Amplification preferably results in extension of the annealed forward primer from its 3' end towards the 5' end of the target sequence. Amplification preferably results in extension of the reverse primer from its 3' end towards the 5' end of its target sequence. Preferably further cycles of amplification result in extension of the forward primer sequence towards the 5' end of its target, including the reverse primer sequence. Preferably further cycles of amplification result in extension of the reverse primer sequence towards the 5' end of its target, including one or more or all of the forward primer sequence and particularly the SNP identifying portion, locus specific portion, SNP related portion and further portion.

A portion of the amplified product may be removed and contacted separately with the second set of primers. Contact with the second set of primers may occur in a separate vessel to the contact with the first set of primers. This is particularly preferred where universal primers incorporating molecular beacons are used. Preferably a two tube and/or branched PCR process is used where universal primers incorporating molecular beacons are employed.

The first and second amplifications may occur in the same vessel. The first and second amplifications may occur substantially simultaneously. Preferably the method includes adding one or more of the first set of primers and one or more of the second set of primers to the sample to be amplified prior to conducting amplification cycles.

The one or more first sets of primers may be provided at a concentration of between 20 and 80 nM, more preferably between 40 and 60 nM and ideally at 50 nM +/−5%. Preferably the primers which do not compete and/or for which site overlap does not occur are provided at these levels. Where primer competition could occur and/or where primer site overlap occurs preferably the primer's relative concentrations are balanced. The reverse primer concentration for such a simultaneous process may be between 75 nM and 125 nM, for instance 100 nM +/−10%.

The second set of primers may be provided at a concentration of between 20 and 80 nM, more preferably between 40 and 60 nM and ideally at 50 nM +/−5%. The amount of the second set of primers added may be defined by Cn×L, where Cn is the concentration of the primers and L is the number of loci under consideration +/−2 and ideally is the number of loci under consideration, particularly where L is less than 100 or even less than 50. Preferably the maximum second set of primers concentration is 1000 nM.

Particularly where the first and second sets of primers are present together, it is preferred to provide the second set of primers and first set of primers at a concentration ratio of at least 5:1. A ratio of at least 10:1, more preferably at least 20:1 and ideally at least 30:1, second set concentration: first set concentration may be provided. The first set may be provided at a concentration of between 5 and 400 nM, more preferably between 10 and 200 nM. The second set may be provided at a concentration of between 300 nM and 5000 nM, more preferably between 400 and 4000 nM.

The amplified product may be contacted with the second primer set by mixing the sample and primers together.

The second set of primers may include one, two, three or four forward primers. A reverse primer may be present, but the second set of primers may lack a reverse primer.

The invention may only provide one second set of primers provided.

In one embodiment of the invention preferably the one second set of primers consisting of two forward primers and a reverse primer. One or more, preferably all, of the second sets of primers may include two forward primers and a reverse primer. One of the forward primers of the second set preferably includes a sequence which anneals to the SNP incorporating strand on the 3' side of the SNP. The reverse primer of the second set preferably includes a sequence which anneals to the 3' side of the base pairing to the SNP. More preferably one of the forward primers includes a sequence which anneals to the 3' side of the SNP repeat. Preferably the other forward primer or primers does not anneal.

In the one embodiment of the invention the second set of primers may include one or more primers including a second further portion. Preferably the forward primers are so provided. Preferably the second further portion is provided with a second SNP identifying portion and/or more preferably an SNP repeat identifying portion. The second SNP or SNP repeat identifying portion may be attached to the 3' end of the second further portion, particularly in the case of forward primers. The 5' end of the forward primer is preferably provided with a distinctive unit.

In the one embodiment of the invention the second further portion preferably includes a sequence which pairs to the sequence of the amplified product in the vicinity of the SNP identifying portion and/or, more preferably, SNP repeat related portion thereof. More preferably the further portion sequence adjacent to the SNP related portion, ideally up to and including the nucleotide before the SNP related portion matches the sequence of the amplified product adjacent to the SNP repeat, ideally up to and including the nucleotide before the SNP repeat. Preferably the forward primers of a second set of primers are provided with identical sequences for the second further portions.

In an alternative embodiment of the invention it is preferred that the one second set of primers consists of one forward primer and one reverse primer. One or more, preferably all, of the second set of primers may consist of one forward primer and one reverse primer. Preferably the forward primer of the second set includes a sequence which anneals to the SNP incorporating strand on the 3' side of the SNP. Preferably the reverse primer of the second set includes a sequence which anneals to the 3' side of the base pairing to the SNP. Most preferably the forward primer includes a sequence which anneals to the sequence which pairs to the sequence produced by the copying of the further portion of the forward primer and/or which corresponds to the sequence of the further portion of the forward primer of the first set.

In the alternative embodiment of the invention, the second set of primers may include a primer including a second further portion and more preferably consisting of a second further portion. Preferably the forward primer is so provided. Preferably the second further portion is provided with a sequence which pairs to the sequence of the amplified product in the vicinity of the sequence which pairs to the further portion of the forward primer of the first set. More preferably, the second further portion includes a sequence which matches the sequence of the first further portion and/or pairs to the sequence of the amplified product matching the first further portion.

Preferably the sequence of the second further portion does not anneal to, and particularly does not match, the sequence of any published part, ideally any part, of the entire DNA sequence of the entity from which the DNA containing the SNP under investigation was obtained, for instance Homo Sapiens. The inability of the sequence of the second further portion to amplify human DNA is a particularly preferred feature. Preferably the forward primers of a second set of primers are provided with identical sequences for the second further portion.

In the one embodiment of the invention the second SNP related portion is preferably a single nucleotide or two nucleotides.

In the one embodiment of the invention preferably the second SNP related portion of one primer of the second set is, or includes, a nucleotide which is identical to the SNP identifying portion and/or SNP related portion of a primer of the first set. Preferably another, ideally the other, primer of the second set has a second SNP related portion which is, or includes, a nucleotide which is identical to the SNP identifying portion and/or SNP related portion of another, ideally the other, primer of the first set.

In the one embodiment of the invention where a single nucleotide forms the second SNP related portion, the second SNP related portion may be a C nucleotide when amplifying a target in which the SNP or SNP repeat is a G nucleotide. The second SNP related portion may be a G nucleotide when amplifying a target in which the SNP or SNP repeat is a C nucleotide. The second SNP related portion may be a T nucleotide when amplifying a target in which the SNP or SNP repeat is an A nucleotide. The second SNP related portion may be an A nucleotide when amplifying a target in which the SNP or SNP repeat is a T nucleotide. The second SNP related portion for one forward primer of a second set may be one of C or G or T or A with the second SNP related portion of another primer of the second set being one of C or G or A or T, but different to the second SNP related portion of the first primer of that set where the SNP or SNP repeat under investigation could be any two of C or G or T or A nucleotides.

In the one embodiment of the invention the second SNP related portion may be formed of two nucleotides. Preferably the end nucleotide of the two matches with the nucleotide of the SNP or SNP repeat of interest. Preferably the nucleotide adjacent to the end nucleotide of the second SNP related portion is a mismatch with the base adjacent to the SNP or SNP repeat in the target sequence.

In the one embodiment of the invention preferably the second SNP related portion forms the 3' end of the forward primers of the second set.

An exonuclease digestion prevention unit may be provided towards the 3' end of the forward primer or primers of the first and/or second set. The exonuclease digestion prevention unit may be phosphorothioate. The exonuclease digestion prevention unit may be provided at the end of the second further portion and/or the junction of the second further portion and second SNP related portion.

Preferably the second further portion and/or second SNP related portion of the forward primer and/or of one of the forward primers anneals to the 3' side of the SNP or SNP repeat. Preferably the second further portion and/or second SNP related portion of another, ideally the other, of the forward primer and/or of the forward primers does not anneal to the 3' side of the SNP and/or SNP repeat. In one embodiment of the invention preferably the annealing primer anneals due to a match between the second SNP related portion and the SNP repeat and/or adjacent sequences. Preferably the non-annealing primer does not anneal due to a mismatch between the second SNP related portion and the SNP repeat. In an alternative embodiment of the invention preferably the annealing primer anneals due to a match between the second further portion and a sequence which paired to the first further portion.

The second amplification is preferably performed by PCR. The amplification preferably involves between 18 and 30 cycles, more preferably 20 to 25 cycles.

One or more of the primers of the first and/or second set may be provided with one or more portions which are complimentary to one or more portions on one or more of the other primers in that set. The complimentary portion or portions are preferably provided in the further portion of the primers of the first set. The complimentary portion or portions are preferably provided in the second further portion of the primers of the second set. Preferably a complimentary portion is provided on each of the primers of a set.

Preferably at least two complimentary portions are provided on each of the primers of a set. Preferably a complimentary portion is provided at the 3' end of a primer, ideally all the primers. Preferably a complimentary portion is provided at the 5' end of a primer, ideally all of the primers. Preferably the 3' end complimentary portion of one primer is complimentary to the 5' end complimentary portion of another primer, ideally all the other primers of the set and/or both sets. Preferably the 5' end complimentary portion of one primer is complimentary to the 3' end complimentary portion of another primer, ideally all the other primers of the set and/or both sets. A locus specific portion may be provided on the further portion including the complimentary portion or portions, particularly on the 3' end. The further portion and/or second further portion may include a sequence matching the sequence of the locus under consideration, particularly provided between two complimentary portions. The complimentary portions may be at least 3 nucleotides long, more preferably between 3 and 20 nucleotides long. The complimentary portions are preferably both of the same length. The complimentary portions may form between 5 and 40% of the further portion and/or second further portion. One, two, three or four primers of a set may be provided in this way. Preferably the reverse primer or primers are similarly provided.

The further amplified product, or a portion thereof, may be removed from the vessel in which the amplification is performed to examine the one or more characteristics. Alternatively or additionally, the one or more characteristics may be examined with the further amplified product in the vessel in which amplification is performed.

The one or more characteristic of the further amplified product may be examined by means of the presence and/or absence of a distinctive unit in the further amplified product. The distinctive unit may be incorporated in the farther amplified product or be associated there with. The distinctive unit may be introduced during the amplification process and/or in a subsequent step. The subsequent step may comprise hybridisation, for instance, of a component to the SNP base. The component may be a dideoxynucleotide, particularly a dideoxynucleotide incorporating a distinctive unit such as a dye.

The distinctive unit may be a dye label or colour producing molecule.

The distinctive unit may be a sequence of DNA, for instance a molecular beacon. The sequence of DNA, for instance a molecular beacon, may comprise a sequence of DNA incorporating a dye molecule. The sequence of DNA may be a single strand. The sequence of DNA may be looped by joining one part of the sequence to another. Preferably the dye molecule is in the loop, still more preferably in one part of the sequence which is joined to another. Preferably the dye molecule is in proximity with a quencher molecule. Preferably the quencher molecule prevents the dye molecule characteristic, for instance fluorescence, being visible. Preferably the dye molecule becomes visible, for instance fluorescent, upon activation. Preferably activation is caused by primer extension into the sequence of the molecular beacon. Activation preferably occurs through the opening of the loop. The molecular beacon sequence may be F-ACGCGCTCTCTTCTTCTTTTGCGCG-Q where F is a distinctive unit such as a dye, and Q is a quenching unit or vice versa. Preferably the parts of the molecular beacon sequence which join to one another are the stems ACGCGC from the 5' end and GCGCG from the 3' end. Preferably the universal primer incorporating molecular beacon does not contain phosphorothioate bonding. Preferably none of the second set of primers contain phosphorothioate bonding. Ideally none of the first or second primers contain phosphorothioate bonding. Where molecular beacons are used, the amplification product may be examined for one or more characteristics in the amplification reaction vessel. For instance, the Roche Light Cycler™ or other such instruments may be used for this purpose.

The distinctive unit may be visible under daylight or conventional lighting and/or may be fluorescent.

The distinctive unit may be an emitter of radiation, such as a characteristic isotope.

The distinctive unit is preferably provided at the 5' end of one or the primers, more preferably on a forward primer and ideally with a different distinctive unit for the other forward primer of the second set.

Preferably the distinctive unit is indicative of the nucleotide present at the SNP. Preferably a different distinctive unit is present if one nucleotide is present at the SNP and than if the other nucleotide is present at the SNP. Different distinctive units may be provided for indicating the SNP at one locus when compared with the distinctive units for indicating the SNP present at a different locus.

The examination may involve separating the further amplified product relating to one SNP from the further amplified product from one or more other SNP's. Preferably the further amplified products for each SNP are separated from one another. Electrophoresis may be used to separate one or more of the further amplified products from one another. The further amplified products may be separated from one another based on size of the further amplified products, for instance due to the different length of the further amplified products.

The examination may involve analysing the response of the further amplified product, for instance in the vessel in which amplification was performed, to radiation of various wavelengths, for instance fluorescent light.

The examination may involve the use of micro-fabricated arrays.

The further amplified product may be contacted with one or more components retained on a solid support. One or more of the components may be an oligonucleotide, preferably with its 5' end tethered to the support. Preferably the oligonucleotide has a sequence which pairs/anneals with the sequence of at least one, ideally only one, of the further amplified products.

In an embodiment the oligonucleotide may have a sequence which pairs/anneals with the sequence of at least one, ideally only one, of the further amplified products up to the base before the base which is the SNP site. Only a portion of the further amplified product may pair/anneal to the oligonucleotide. Preferably a particular further amplified product type pairs/anneals to a particular oligonucleotide.

In an another embodiment, the oligonucleotide may have a sequence which pairs/anneals with the sequence of at least one, ideally only one, of the further amplified products along the sequence corresponding to the locus specific portion and the further portion. Preferably the further portion of the further amplified product includes a distinctive unit. The distinctive unit is preferably a dye. Preferably a different dye is present on each different further amplified product.

A plurality of such components, such as a plurality of oligonucleotides may be provided. A plurality of different oligonucleotides may be provided with each having a sequence which pairs/anneals to a further amplified product, ideally only one such product. It is particularly preferred that each oligonucleotide type pairs/anneals to a different further amplified product type from the others. The plurality of different types of oligonucleotides may be provided at a plurality of different, ideally discrete locations on the support.

The solid support may be glass, silicon, plastics, magnetic beads or other materials.

In an embodiment one form of the invention, the oligonucleotide and paired/annealed further amplified product may be contacted with one or more further components. Preferably one or more of the further components includes a dideoxynucleotide. Preferably one or more of the further components includes a distinctive unit, such as a dye. Preferably different further component types include different distinctive units. Two or more components comprising two or more different dideoxynucleotides with a different distinctive unit attached to each may be provided. The dideoxynucleotides may be A, T, C or G. Three or four dideoxynucleotides may be provided, preferably each with a different distinctive unit.

One or more, preferably only one of the further components may selectively attach to the SNP base and/or 3' end of the oligonucleotide. Preferably the selectivity of the attachment is based on the pairing of part of the further component's identity with the SNP base identity, such as the pairing of the dideoxynucleotide identity with the SNP base identity. Preferably the pairing incorporates the distinctive unit in the structure. Preferably the pairing incorporates the distinctive unit in the structure. Preferably non-pairing further components and their distinctive units are not incorporated in the structure.

The identity of the distinctive unit attached to the component in the structure is preferably investigated. Preferably the identity of the further component and/or the identity of the SNP is derived from the identity of the distinctive unit.

In another form of the invention, the oligonucleotide and paired/annealed further amplified product may be contacted with one or more additional components. The one or more additional components may be one or more further oligonucleotides. Preferably one or more of the additional components includes an end base, preferably at its 5' end. Preferably one or more of the additional components includes a distinctive unit, such as a dye. Preferably different additional component types include different distinctive units. The additional components may comprise two or more different further oligonucleotides with a different distinctive unit and/or end base attached to each. The end base of the further oligonucleotides may be C, G, A or T. Three of four further oligonucleotides may be provided, preferably each having a different distinct unit and/or end base.

One or more, preferably only one, of the further oligonucleotides may selectively attach to the SNP base and/or 3' end of the tethered oligonucleotide. Preferably the selectivity is based on the pairing of the further oligonucleotide's end base identity with the SNP base identity. Ligase may be provided in contact with the tethered oligonucleotide and/or further oligonucleotide and/or further amplified product. Preferably ligation occurs where the SNP base and end base pair, thereby incorporating the distinctive unit in the structure. Preferably non-pairing further components and the distinctive units are not incorporated in the structure.

The identity of the distinctive unit attached to the component in the structure is preferably investigated. Preferably the identity of the additional component and/or the identity of the end base of the additional component and/or the identity of the SNP is derived from the identity of the distinctive unit.

In yet another embodiment of the invention the further amplified product may incorporate an attachment unit. Preferably the attachment unit facilitates attachment of the further amplified product to a solid support. The solid support may be glass, silicone, plastics, magnetic beads or other materials. Preferably attachment is affected by means of a covalent bond. The attachment unit may be an amino group, preferably an amino group provided at the 5' end of the further amplified product. It is preferred that the solid support is an epoxy-silane treated support in such cases. The attachment unit may be a phosphorothiate unit, ideally provided at the 5' end of the further amplified product. In such a case, attachment to a bromo-acetomide treated solid support is preferred.

The further amplified product, attached to a solid support, is preferably contacted with one or more probes preferably having a different sequence from one another, at least in part. Preferably each probe has a common sequence portion to each other probe. It is particularly preferred that this common sequence portion correspond in sequence to the locus specific portion of the further amplified product. Preferably the probes incorporate at least one different sequence portion compared with one another. Preferably the different portions, for at least one of the probes, corresponds to the universal primer portion sequence of the further amplified product. It is preferred that contact of the probes with the further amplified product results in hybridisation of one of the probes to the further amplified product, ideally with no hybridisation of the other probe or probes. Preferably each probe has a distinctive unit attached, such as a dye unit. Preferably different distinctive units are used for each different probe.

The sample may be compared with another sample. The comparison may be based on comparing one or more of the one or more characteristic of the further amplified products for each sample. The samples may be compared to confirm a match in the characteristic between the samples. The samples may be compared to eliminate a match in the characteristic between the samples. The occurrence of the one or more further characteristic for one or more SNP's may be compared with information on the frequency of occurrence of the one or more further characteristic for the one or more SNP's in a population. The population may be a representative sample of the population of a country, an ethnic group or database.

The third and/or fourth aspects of the invention may include one or more of the features, options or possibilities set out elsewhere in this document, including, but not limited to the first and/or second aspects of the invention and the statements that follow them.

BRIEF DESCRIPTION OF THE SEVERAL VIEWS OF WE DRAWINGS

Various embodiments of the invention will now be described, by way of example only, and with reference to the accompanying drawings in which:

FIG. 2b illustrates a second forward primer suitable for use in that technique and intended for use with the primer of FIG. 2a;

FIG. 4b illustrates a second universal forward primer for use in the second stage of the technique and intended for use with the primer of FIG. 4a.

Figure 1A:
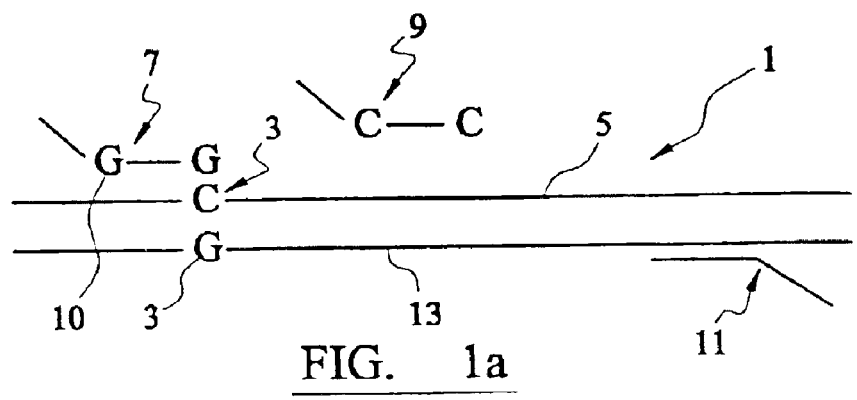
FIGS. 1a to 1e illustrate the various parts of the first stage of a process in which the present invention can be utilised.
Figure 1B:
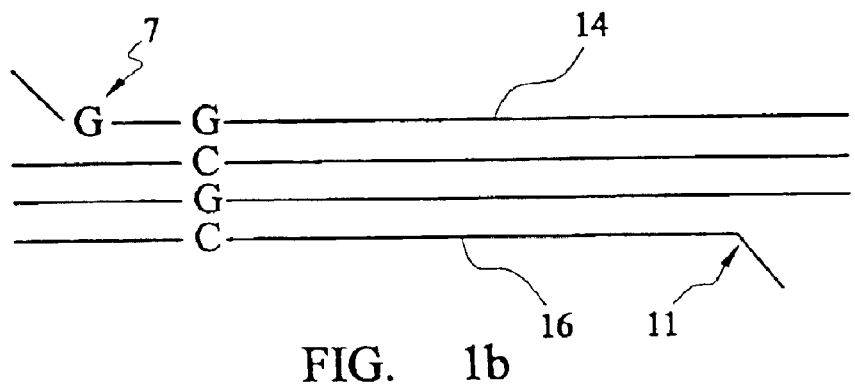
Figure 1C:
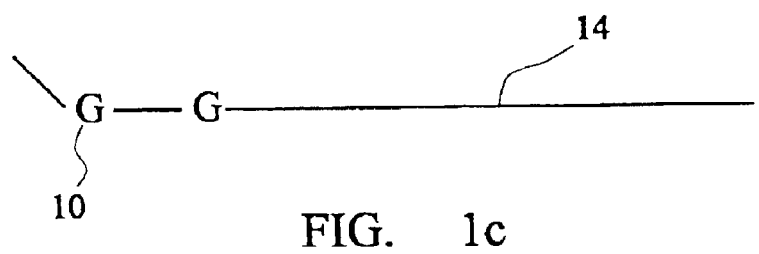
Figure 1D:
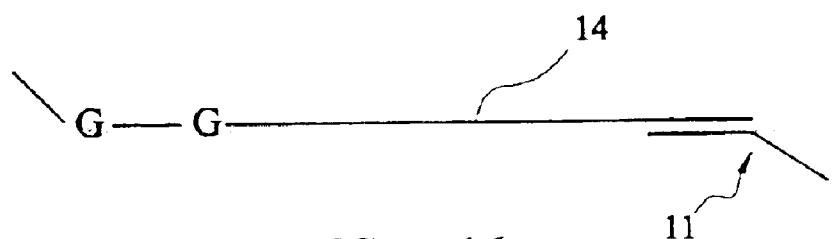
Figure 1E:
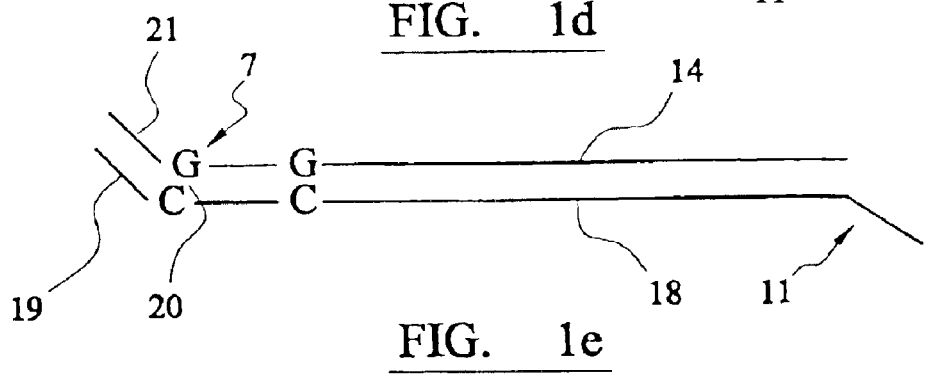

The nucleotide sequence of humans and other biological entities is in a large part consistent between individuals. Locations are known, however, at which variation occurs. One such form of variation is known as single nucleotide polymorphisms or bi-allelic markers, where the identity of a single nucleotide at a specific location is one of four possibilities from any of the four bases available, A, T, G or C. In many cases the variation is only bi-allelic and hence only one or two possibilities applies. Thus, some individuals may have a sequence incorporating a C base at a particular position, whereas other individuals will have a G base at that position; the surrounding sequences for both individuals being identical.

Medical diagnostics, forensic investigations and other DNA tracing applications make use of such single nucleotide polymorphisms (SNPs) for identification purposes. As the variation between individuals can only be between one of two options, a very substantial number of such locations, loci, must be considered for a statistically significant result, for instance the statistical significance of a match between a collected sample and an individual's makeup to be obtained.

Investigating such a large number of loci, frequently several hundred, on an individual basis is extremely time consuming. To reduce the time taken, it might be desirable to construct multiplexes which allow a substantial number of loci to be investigated simultaneously based on PCR or other amplifying techniques. The design of reliable constructs for a large number of loci, however, is extremely difficult due to problems in interactions between the primers needed for the different loci, different conditions for suitably efficiency amplification of the different primers and a variety of other issues.

The technique of the WO01/07640 is designed to simplify SNP based and other investigations, and particularly to facilitate the rapid development of multiplexes suitable for investigating a large number of such loci simultaneously, due to the flexibility offered by the techniques described therein. The present invention provides improvements in the cycling regimes used to achieve amplification in the amplification stages of those techniques, amongst others.

The techniques of WO01/07640 are based around two amplification stages, generally achieved through PCR, with both of the stages offering specifity in terms of the SNPs identified and amplified. The two amplification stages can be conducted separately or simultaneously and the amplification products can be analysed in a variety of ways.

FIG. 1 illustrates, according to one embodiment of the technique, a series of stages involved in the first amplification process based around a target template 1 with a potential C or G single nucleotide polymorphism 3 in one strand 5 of that target template 1. As illustrated in step A, the target template strand 5 of the particular individual under consideration has a C nucleotide at the SNP site 3.

The first step in this amplification stage involves contacting the template target 1 with two different forward primers 7 and 9, and a reverse primer 11. The forward primers 7 and 9 are locus specific primers, described in more detail below.

Forward locus specific primer 7 is terminated by a G nucleotide thus rendering it a match with the C nucleotide at the SNP site 3 and resulting in annealing of that primer 7 with the strand 5. The reverse primer 11 is non-specific and anneals to the other strand 13 of the template 1 at the appropriate location.

In step B, the specific forward primer 7 and the reverse primer 11 extend to produce the strands 14 and 16 through primer extension.

Denaturation of the strands results in the separation of the strands 5, 13 from their respective copied strands 14 and 16. The copied strand 14 only is shown in step C and the illustration of the subsequent steps.

Subsequent primer annealing, step D, is then performed again using the two forward primers 7, 9 and reverse primer 11. As we are considering strand 14 it is the reverse primer 11 which attaches to the strand 14 due to its sequence. The specific forward primer 7 would attach to strand 16, once again annealing in alignment with the site of the SNP 3 in that strand's sequence, not shown.

In subsequent primer extension, step E, the reverse primer 11 extends the sequence of new strand 18 with the appropriate sequence given the sequence of strand 14, including the extension to produce tail portion 19 which arose as the strand 14 included the tail portion 21 of the forward specific primer 7. Due to the G base in the sequence of strand 14, the new strand 18 includes an opposing C base so as to match the identity of the SNP at site 3 in original strand 5. Due to the G base in the sequence of strand 14, due to the SNP related base 10, the new strand 18 includes an opposing C base 20 so as to match the identity of the SNP related site 10 in the originally copied strand 14.

Repetition of steps A through E over 20 to 25 cycles produces many millions of copies of sequences incorporating the same SNP identity, SNP repeat and surrounding sequence as the target template 1.

Figure 2A:
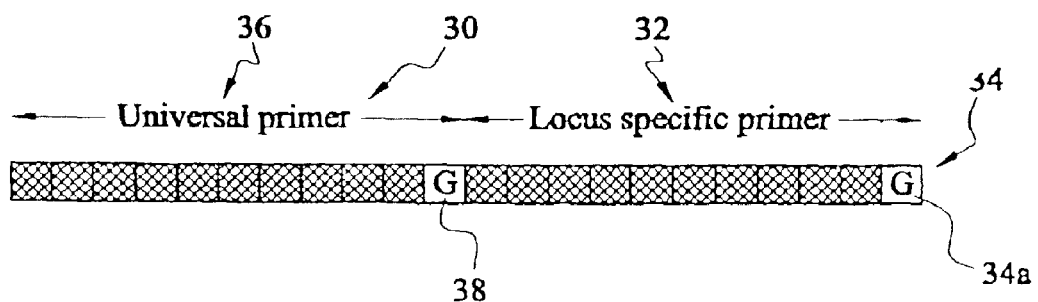
FIG. 2a illustrates one forward primer suitable for use in that technique.
Figure 2B:
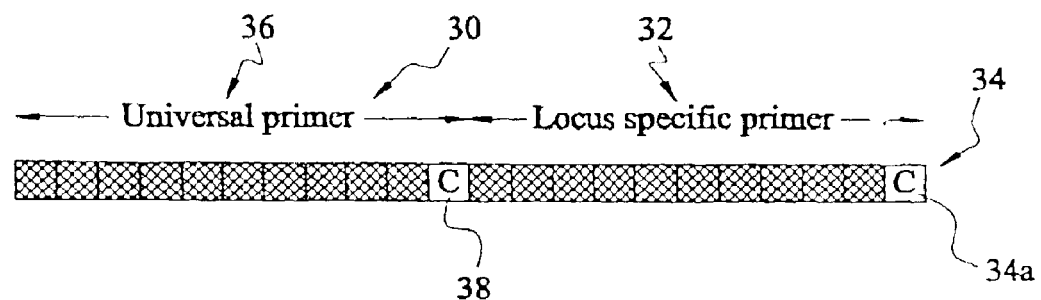
Figure 3A:
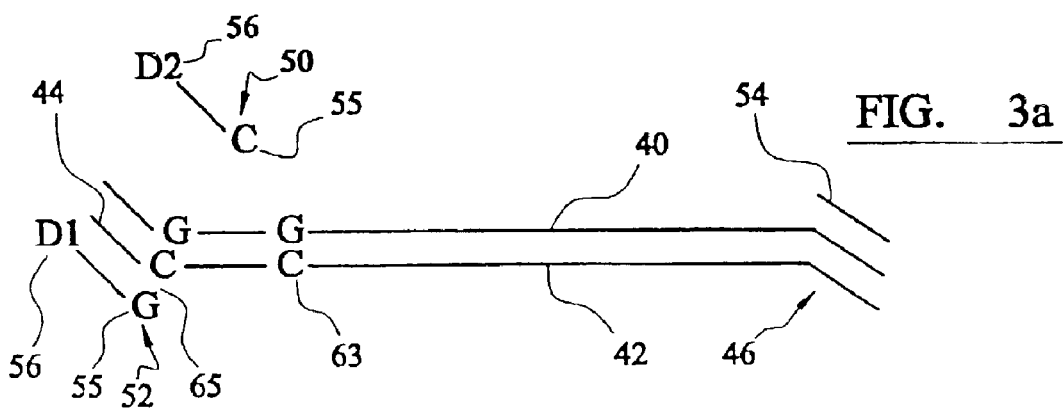
FIGS. 3a to 3e illustrate the various parts of the second stage of a process suitable for incorporating the present invention.
Figure 3B:
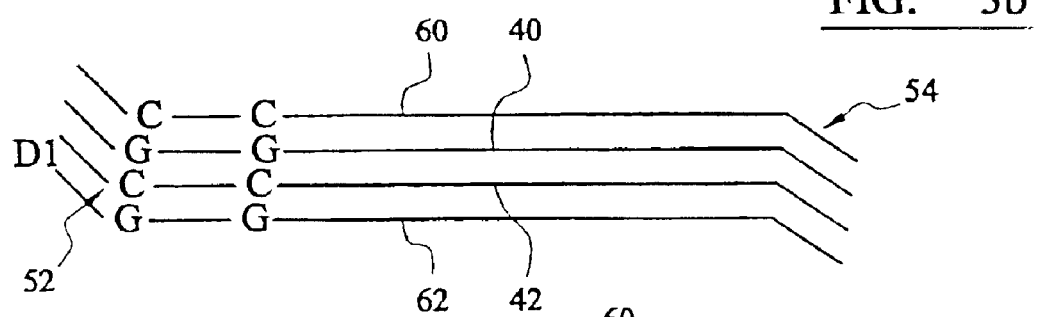
Figure 3C:
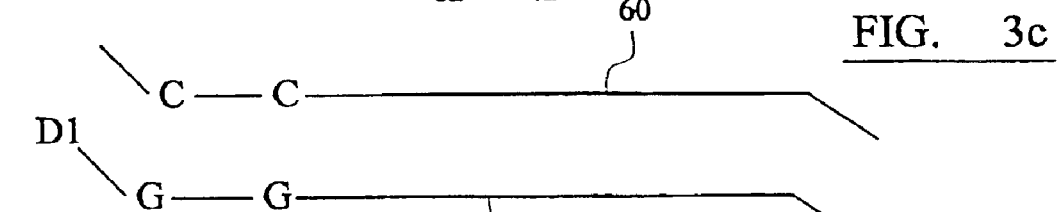
Figure 3D:
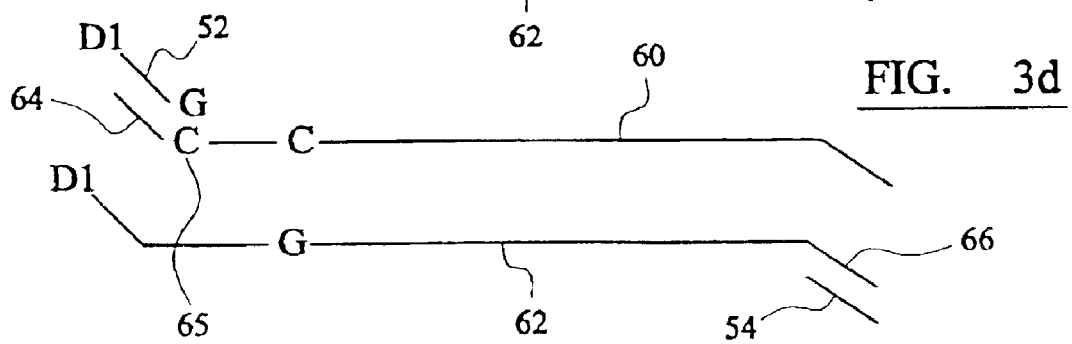
Figure 3E:
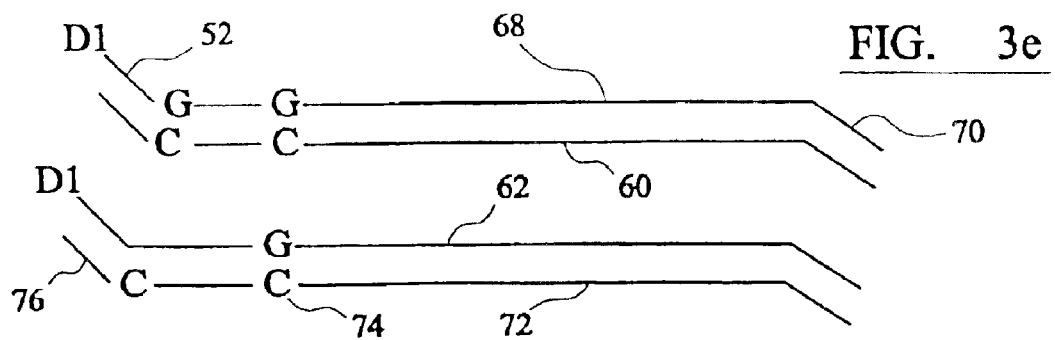

FIGS. 2a and b illustrate two locus specific forward primers, suitable for use in the stage detailed above, for use in investigating an SNP which could be either G or C. Each of the locus specific forward primers 30 consists of a locus specific portion 32 which has a sequence corresponding to the sequence of the loci under consideration up to the SNP site. The 3' end 34 of the locus specific forward primers ends in a G nucleotide 34a for one of the primers, FIG. 2a, and in a C nucleotide 34b for the other primer, FIG. 2b. Due to this different nucleotide used at the position corresponding to the SNP, then depending upon the identify of the SNP actually encountered, one of the locus specific forward primers will anneal thereto, but the other will not. Thus it is the forward primer of FIG. 2a which anneals to the target in the example of FIG. 1. This selectivity in annealing gives consequential specifity in the subsequent amplification cycles of the first stage.

In addition to the locus specific portion 32 the locus specific forward primer 30 includes a "universal" primer portion 36. The "universal" primer portion 36 consists of a nucleotide sequence which is identical for each of the two loci specific forward primers, save for a single nucleotide location 38 at the junction between the universal primer portion 36 and loci specific portion 32 of the primer 30. The nucleotide at the location 38 is identical to the 3' end nucleotide 34 of the locus specific portion 32 of the respective primer 30. Thus, the "universal" primer of FIG. 2a incorporates G in its sequence at location 38 to reflect the G nucleotide present at the 3' end 34. The "Universal" primer portion of FIG. 2b, on the other hand, includes a C at location 38 to reflect the fact that a C nucleotide forms the 3' end 34 of this primer 30.

Whilst it is the locus specific portion 32 of the forward primers 30 which determines whether a primer anneals or not to the target, in the second and subsequent copying stages of the amplification process of stage 1, primer extension causes copying of the "universal" primer portion 36 of the primer sequence also and hence copying of the SNP equivalent nucleotide identity at location 38 too.

Whilst described above in relation to locus specific primers 7, 9, which incorporate SNP related bases 10, the technique is more preferably applied using locus specific primers 7, 9 formed of a locus specific primer portion and universal primer portion without a linking SNP related base. It should be noted in such cases that the universal primer portion has a nucleotide sequence which is different between each of the two forward primers and that the variation in the sequence of the amplification products which is used in subsequent identification arises from this difference.

As previously stated the amplification process of the first stage results in a large number of copy sequences, including the SNP identity reflecting nucleotide and the matching nucleotide at location 38.

In the second stage of amplification, illustrated in FIG. 3, a further specific amplification process is performed. It is much preferred that the second stage of amplification be conducted in the same vessel as the first, substantially simultaneous with the first amplification process. Such a possibility is described in more detail below.

For this stage, an aliquot of the amplification products from the first stage, described above, are taken and contacted with a pair of "universal" forward primers and a "universal" reverse primer. These "universal" primers are described in more detail below.

In step A, the strands 40 and 42 (copy strands which are equivalent to strands 14, 18 produced in the first stage as illustrated above) produced by the first stage 1 are denaturated and contacted with the two "universal" forward primers 50, 52 and reverse "universal" primer 54.

The two "universal" forward primers differ in terms of the 3' terminal end nucleotide 55 and in terms of a dye unit D or other form of label provided on the 5' end 56. The 3' end nucleotide 55 for the forward "universal" primers in this example is either C, "universal" primer 50, or G, "universal" primer 52.

As the strands 40 and 42 represent the outcome of copies of copies of the originals being taken, unlike strands 14, 18, they both have tail portions 44, 46 respectively which arise from the copying of the "universal" primer portions of the locus specific forward primer and reverse primer in the first stage.

The "universal" primers 50, 52 each have a sequence corresponding to the "universal" primer portion 34 of the first stage locus specific primers 30 up to location 38 of the locus specific forward primers 30. At location 55 the forward primers 50, 52 of the second stage have a base corresponding in identity to the identity of the nucleotide pairing to the SNP repeat in the stage 1 process, in one case, and in the other case corresponding to the identity of the other option for the SNP repeat. The nucleotide identity for the "universal" primers 50, 52 at location 55, corresponding to location 38, as thus different for the two primers 50, 52, with one providing one of the options and the other providing the other.

In the illustrated example, primer 50 carries a C and primer 52 carries a G nucleotide at position 55.

The sequence of the primers 50, 52 and particularly the identity at position 55 determines whether or not that primer 50, 52 anneals to the tail portion 44 of the strand 42 or not. In the illustrated case, strand 42 carries the SNP nucleotide C at site 63 as this was a copy of the identity of the SNP at site 3 in the original target strand 5. The C identity is also repeated in the tail portion 44 at site 65 as this was copied due to the copying of the tail of the original primer 7 by the reverse primer 11 in the first stage. As a consequence the sequence of the tail portion 44 of strand 42 provides an annealing site for "Universal" primer 52, but not primer 50. The reverse primer 54 anneals to the tail portion 46 of strand 40 due to the sequence matching.

In alternative, preferred techniques, the sequence of the primers 50, 52 possesses the dye unit D, in the form of dye unit D1 or different dye unit D2, or other form of label, but lacks the 3' end nucleotide identified in the preceding paragraphs. In this case the differences in the tail portion sequences due to the different universal primer portion sequences of the two different primers of the first stage give rise to the annealing of the primer where a match occurs, but not in the other case. As a consequence the dye unit D or other identity indicating label is introduced. In a still further alternative technique the dye unit D or other form of label is omitted from both the universal forward primers of this second stage and determination of the identity is achieved through a third stage as illustrated in FIGS. 12a through 12e, for example, of WO01/07640. Again it is the matching versus non-matching universal primer sequences which are important in that situation.

Primer extension, step B, results in the production of strand 60 by matching strand 40, including SNP site copy C, and in the production of strand 62, including the match for the SNP, G, by matching strand 42 by the "universal" reverse primer 54 and specific "universal" forward primer 52 respectively. The SNP repeats are also copied.

Thermal denaturation is then used to separate the strands, step C, and from here on strands 60 and 62 only are considered although similar processes apply to the other strands too.

In annealing step D, the specific "universal" forward primer 52 anneals to the tail 64 of strand 60 due to the presence of a C nucleotide at the relevant position 65 in strand 60 and the consequential pairing to the "universal" forward primer 52. The reverse primer 54 anneals to the tail portion 66 of the strand 62.

In the further extension step E, the forward primer 52, which brings with it the label D1, extends the sequence of new strand 68, including tail portion 70. The reverse primer 54 extends the sequence of new strand 72, (thereby reproducing the SNP identity at site 74), including tail portion 76, (thereby reproducing the nucleotide corresponding to the SNP repeat 75 in that part too). Strand 62 already incorporates the label D1 from its start as the primer 52 in step A.

Once again, repeating steps A to E gives substantial amplification of the sequences and produces a great number of sequences label with a dye D1, the dye being selectively taken up as only one primer anneals and thus takes the dye into the sequence with it.

Figure 4A:
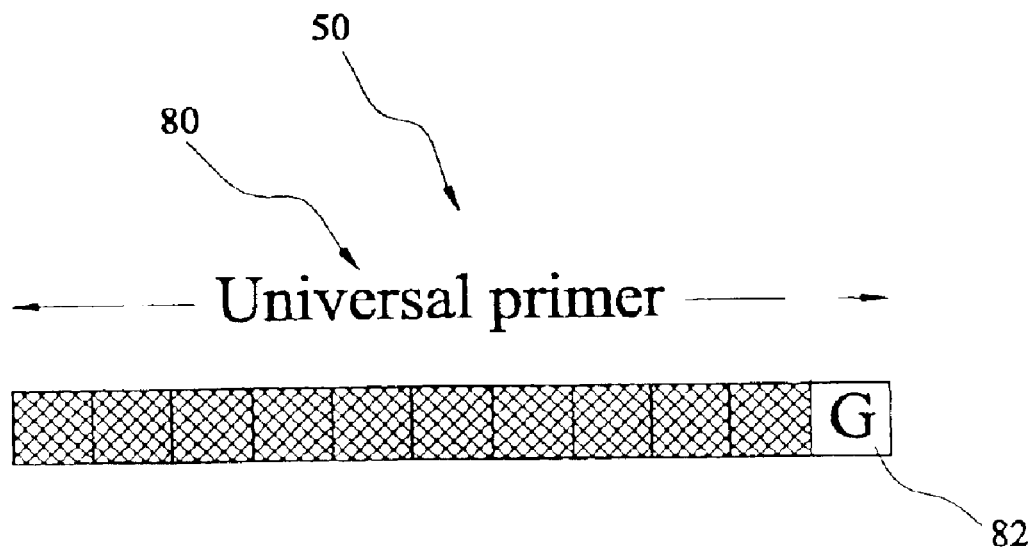
FIG. 4a illustrates a universal forward primer suitable for use in the second stage of the technique.
Figure 4B:
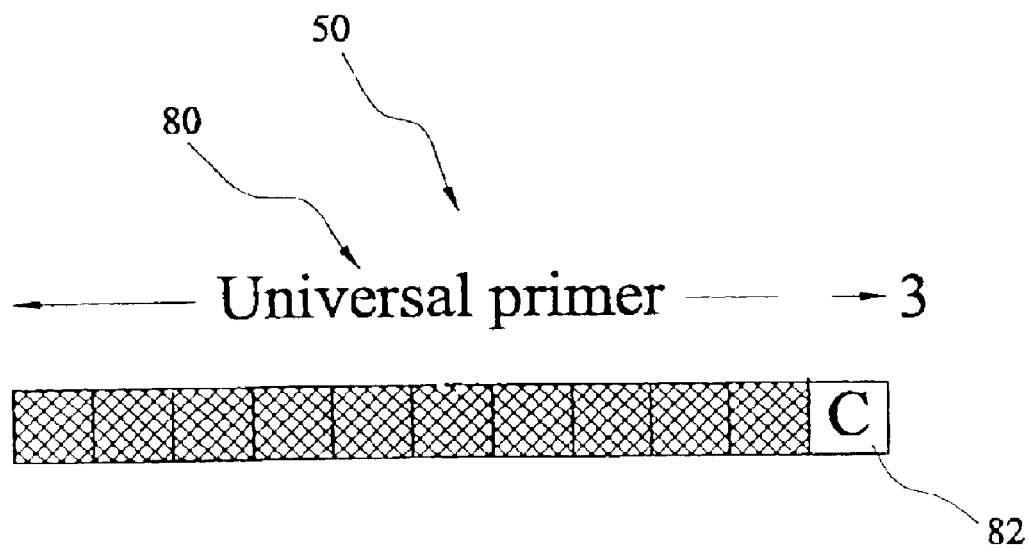

As described above, the second stage of the process uses a pair of "universal" primers on their own, illustrated in FIGS. 4a and 4b. These consist of a portion 80 having a sequence identical with the "universal" primer portion 32 of the locus specific primers 30 up to the single nucleotide variation at the end of the "universal" primer portion 32. The ends 82 of the universal primers of FIGS. 4a and 4b are different from one another and have an identity consistent with one of the two SNP possibilities, as is the case for the primers of FIGS. 2a and 2b. Thus, one "universal" primer 52, FIG. 4a, is provided with G at its terminal 3' end 82 and the other "universal" primer 50, FIG. 4b, is provided with C at its terminal 3' end 82.

During stage 2 of the process, these "universal" primers will selectively anneal to the amplification products of the first stage depending upon whether the tail portions extended and amplified during that stage incorporates the G or C variation.

Of course, equivalent primer types could be used with T or A variations in the above mentioned processes to investigate an SNP having potential T or A variation.

In the case of the alternative techniques, the universal primers will selectively anneal to the amplification products of the first stage depending upon whether the tail portions have a sequence matching to the first universal primer or second universal primer.

The different "universal" forward primers are provided with different labels/markers, in this case a JOE dye label and an FAM dye label respectively. The dye labels are provided at the 5' end of the forward primer in the second stage of the process. Of course, other different dyes and other forms of marking, such as radio nuclides could be used.

A key feature of the technique is that the primers in the first set differ from one another only in terms of a single nucleotide as far as the part of the sequence which is intended to anneal is concerned in the first part of the first stage. Taking the instance where the SNP could be a C or a G nucleotide, the first set of primers will be a pair of primers, both primers being the same length (between 15 and 35 bases long) and both being identical in their sequence apart from the last base. The last base will be a C in one case (to correctly anneal to a DNA sequence exhibiting the G polymorphism) and a G in the other case (to correctly anneal to a DNA sequence exhibiting the C polymorphism). The more significantly different universal primer sequences in the preferred amplification techniques of course are not involved in the annealing at this time. Because of this similarity there is little selectivity in the initial annealing process when the two primers are contacted with the DNA. Out of 100 DNA strands exposed to the excess of primers, for instance, around 50 will correctly anneal with a primer having an end base pairing to the SNP and around 50 will anneal with a primer having an end base which is the same as the SNP.

In the conventional amplification process for example as set out in WO01/07640, the DNA is contacted with the primers and exposed to a high denaturing temperature, around 94° C. to split the strands; then exposed to an annealing temperature of around 61° C. to promote primers annealing to the strands; then exposed to an extension temperature of 72° C. to make the complimentary strand copy. A high denaturing temperature is then applied as the first part of the next cycle. The cycle is then repeated through 6 or so cycles with denaturing being followed by annealing being followed by extension being followed by denaturing and so on.

The problem is that only 50 or so of the 100 strands will extend using this type of amplification in the first cycle with a very large impact on the number of copies in the end product as a result.

The present invention uses the realisation that an incorrect annealing can be removed using a relatively low temperature whilst leaving a correctly annealed primer in place so that it extends and the realisation that increasing the level of correct annealing in the early cycles is crucial to effective amplification.

An exemplary amplification has (following TAQ-GOLD activation at 95° C. for 11 minutes) three phases, with the principal benefits arising from the revised first phase. In effect the first phase achieves the annealing, extension process set out in FIGS. 1a and 1b; the second phase achieves the process set out in FIGS. 1c, 1d and 1e; and the third phase achieves the process set out in relation to FIG. 3. Thus the first stage involves the first and second phases, and the second stage involves the third phase of the cycling regime now described by way of example.

Phase 1
94° C. for 30 seconds—to denature
60° C. for 15 seconds—to anneal
72° C. for 15 seconds—to remove incorrectly annealed primers and extend others
60° C. for 15 seconds—to anneal
72° C. for 15 seconds—to remove incorrectly annealed primers and extend others
60° C. for 15 seconds—to anneal
72° C. for 15 seconds—to remove incorrectly annealed primers and extend others
Repeated for 2 to 6 cycles.

In the prior art, of 100 strands present in the original DNA sample around 50 correctly anneal and contribute to extension and copying in the subsequent cycles and around 50 incorrectly anneal and would make no further contribution.

In the present invention, however, the extension temperature which follows the first annealing temperature removes those incorrectly annealed primers (without removing the correctly annealed primers which would need a higher temperature to remove) and thus frees them for the next annealing temperature. The correctly annealed primers extend during the extension temperature. The overall result, out of a sample of 100 strands, is that around 50 have been extended by the first anneal/extend temperature pair and the other 50 or so have incorrectly annealed but then been freed up by the extension temperature. The presence of another annealing temperature immediately after this (as opposed to a much higher temperature denaturing step) means that around 25 of those strands then anneal to the correct primer on the same equal likelihood basis and will then be extended upon exposure to the extension temperature which follows (the other 25 or so incorrectly anneal again, but are again freed up by the extension temperature). Further incorrect primer removal and annealing temperature repeats increase the number of the original strands which have the correct primers attached and hence extend. The overall result of Phase 1 is to ensure as much as possible of the DNA of interest is extended (on average 87% of the strands during the first Phase 1 cycle alone—using three pairs of annealing and extension temperatures) and thus contributes to the main amplification process in Phase 2; without which the end number of copies would be significantly lower for the same number of amplification cycles. Because the times spent at each temperature are relatively short the Phase 1 cycles take little time to perform compared with the overall time of the three phases and initial activation, but has substantial benefit.

Phase 2
94° C. for 30 seconds—to denature
76° C. for 105 seconds—to anneal and extend
Repeated for 29 to 33 cycles.

The denaturing temperature ensures that the strands separate to be available for the next copying stage. The annealing temperature is higher than in previous proposals, which whilst allowing annealing to occur, reduces incorrect primer annealing. A significant reduction in primer-dimer formation is also provided as a result, together with significant inhibition of the formation of labelled products arising from the second set of primers which are intended to be active in Phase 3. The higher temperature still gives annealing of the correct primer because the primer is now annealing along its full length (rather than having a free tail portion). The 76° C. stage duration is also longer than under previous proposals to allow time for annealing and extension to complete.

Phase 3
94° C. for 60 seconds—to denature
60° C. for 30 seconds—to anneal the second set primers
72° C. for 60 seconds—to extend
Repeat for 3 cycles.

During this stage the labelled amplicons are produced for investigation using a technique dependant on the type of label deployed.

The overall result is a technique which maximises sensitivity by using as much as possible of the original DNA in the subsequent amplifications, whilst minimising incorrect annealing or the production of undesired amplification results. The sequence of Phase 1 in particular maximises the number of copies made of the original sample in a quick time period.

What is claimed is:

1. A method of amplifying one or more DNA sequences in a DNA containing sample, the one or more sequences including a single nucleotide polymorphism, the method comprising contacting the sample with a set of primers and providing amplification of the DNA sequences using the primers to give an amplified product, wherein the amplification comprises a first phase and a second phase, the first phase comprising exposing the DNA sample to a denaturation temperature step, followed by an annealing temperature step followed by a correctly annealed primer extension temperature step, these steps being followed, at least, by an annealing temperature step, followed by a correctly annealed primer extension temperature step, these steps occurring prior to exposing the DNA sample to a further denaturation temperature step, the second phase providing one or more cycles of a denaturation temperature step followed by an annealing temperature step and extension temperature step.

2. A method of amplifying DNA in a DNA containing sample, the method comprising contacting the sample with a set of primers and providing amplification of the DNA using the primers to give an amplified product, wherein the amplification comprises a first phase and a second phase, the first phase comprising exposing the DNA to a denaturation temperature, followed by an annealing temperature followed by a correctly annealed primer extension temperature, these being followed, at least, by an annealing temperature, followed by a correctly annealed primer extension temperature, these temperatures occurring prior to exposing the DNA to a further denaturation temperature.

3. A method according to claim 2 in which the DNA is one or more DNA sequences in the DNA containing sample, the one or more sequences includes a single nucleotide Polymorphism, the method includes contacting the sample with a set of primers, the second phase providing one or more cycles of a denaturation temperature followed by an annealing temperature and extension temperature.

4. A method according to claim 2 in which the correctly annealed primer extension temperature step provides a temperature and/or duration which provides extension of a primer with a pairing base to the single nucleotide polymorphism and the correctly annealed primer extension temperature step provides a temperature and/or duration which provides for the removal from an annealed state with the DNA of a primer with an equivalent base to the single nucleotide polymorphism.

5. A method according to claim 2 in which an annealing temperature step of the first phase employs a temperature of 60° C.+/−1° C. and a duration of between 10 and 20 seconds.

6. A method according to claim 2 in which a correctly annealed primer extension temperature step of the first phase is performed at a temperature of between 70 and 76° C.

7. A method according to claim 6 in which a temperature of 72° C.+/−1° C. is used.

8. A method according to claim 2 in which a correctly annealed primer extension temperature step of the first phase is performed for a duration of 10 to 20 seconds.

9. A method according to claim 8 in which a duration of 15 seconds +/−1 second is used.

10. A method according to claim 2 in which the first phase includes 2 to 6 cycles.

11. A method according to claim 2 in which a cycle includes a denaturation temperature step, an annealing temperature step, a correctly annealed primer extension temperature step, a further annealing temperature step and a further correctly annealed primer extension step in that order.

12. A method according to claim 11 in which the further correctly annealed primer extension temperature step is followed by a still further annealing temperature step and a still further correctly annealed primer extension temperature step.

13. A method according to claim 2 in which the first phase includes a denaturation temperature step together with between 2 and 6 pairs of an annealing temperature step and a correctly annealed primer extension temperature step which follow on one from another.

14. A method according to claim 2 in which phase 2 includes one or more combined annealing temperature step and extension temperature steps.

15. A method according to claim 14 in which the combined annealing temperature step and extension temperature step of phase 2 is performed at a temperature of 76° C.+/−1° C.

16. A method according to claim 14 in which the combined annealing temperature step and extension temperature step of phase 2 is performed for a duration of between 60 and 120 seconds.

17. A method according to claim 2 in which phase 2 includes at least 20 cycle.

18. A method of investigating single nucleotide polymorphisms in a DNA containing sample, the method comprising contacting the DNA containing sample with a first set of primers and amplifying the DNA using those primers to give an amplified product, contacting the amplified product with at least a second set of primer, amplifying the amplified product using those second set of primers to give a further amplified product and examining one or more characteristics of the further amplified product, wherein the amplification to give the amplified product comprises a first phase and a second phase, the first phase comprising exposing the DNA sample to a denaturation temperature step, followed by an annealing temperature step followed by a correctly annealed primer extension temperature step, these steps being followed, at least, by an annealing temperature step, followed by a correctly annealed primer extension temperature step, these steps occurring prior to exposing the DNA sample to a further denaturation temperature step, the second phase providing one or more cycles of a denaturation temperature step followed by an annealing temperature step and extension temperature step and wherein the amplification to give the further amplified product involves a third phase, the third phase providing one or more cycles of a denaturation temperature step followed by an annealing temperature step and extension temperature step, the method further including the determination of the identity of one or more of the single nucleotide polymorphisms in the DNA containing sample.

19. A method of investigating a DNA containing sample, the method comprising contacting the DNA containing sample with a first set of primers and amplifying the DNA using those primers to give an amplified product, contacting the amplified product with at least a second set of primers and amplifying the amplified product using those second sot of primers to give a further amplified product and examining one or more characteristics of the further amplified product, wherein the amplification to give the amplified product comprises a first phase and a second phase, the first phase comprising exposing the DNA sample to a denaturation temperature, followed by an annealing temperature followed by a correctly annealed primer extension temperature, these being followed, at least, by an annealing temperature, followed by a correctly annealed primer extension temperature, these occurring prior to exposing the DNA sample to a further denaturation temperature, and wherein the amplification to give the further amplified product involves a third phase, the third phase providing one or more cycles of amplification using a second set of primers.

20. A method of investigating single nucleotide polymorphisms in a DNA containing sample, the method comprising contacting the DNA containing sample with a first set of primers and amplifying the DNA using those primers to give an amplified product, contacting the amplified product with at least a second set of primers, amplifying the amplified product using those second set of primers to give a further amplified product and examining one or more characteristics of the further amplified product, wherein the amplification to give the amplified product comprises the first phase and a second phase, the first phase comprising exposing the DNA sample to a denaturation temperature step, followed by an annealing temperature step followed by a correctly annealed primer extension temperature step, these steps being followed, at least, by an annealing temperature step, followed by a correctly annealed primer extension temperature step, these steps occurring prior to exposing the DNA sample to a further denaturation temperature step, the second phase providing one or more cycles of a denaturation temperature step followed by an annealing temperature step and extension temperature stop and wherein the amplification to give the further amplified product involves a third phase, the third phase providing one or more cycles of a denaturation temperature step followed by an annealing temperature step and extension temperature step, the method further comprising a method of amplification according to claim 4, the method further including the determination of the identity of one or more of the single nucleotide polymorphisms in the DNA containing sample.

21. A method according to claim 2 in which the annealing temperature step of all annealing temperature steps of the first phase employ a temperature of 60° C.+/−1° C. and a duration of between 10 and 20 seconds.

22. A method according to claim 2 in which all correctly annealed primer extension temperature steps of the first phase are performed at a temperature of between 70 and 76° C.

23. A method according to claim 22 in which a temperature of 72° C.+/−1° C. is used.

24. A method according to claim 2 in which all correctly annealed primer extension temperature steps of the first phase are performed for a duration of 10 to 20 seconds.

25. A method according to claim 24 in which a duration of 15 seconds +/−1 second is used.

* * * * *